United States Patent [19]

Huff et al.

[11] Patent Number: 5,160,594

[45] Date of Patent: * Nov. 3, 1992

[54] APPARATUS AND METHODS FOR ISOELECTRIC FOCUSING OF AMPHOTERIC SUBSTANCES INCORPORATING ION SELECTIVE MEMBRANES IN ELECTRODE CHAMBERS

[75] Inventors: G. David Huff; L. Scott Rodkey, both of Houston, Tex.

[73] Assignees: Board of Regents of the University of Texas System, Austin; Ampholife Technologies, Inc., The Woodlands, both of Tex.

[*] Notice: The portion of the term of this patent subsequent to Oct. 16, 2007 has been disclaimed.

[21] Appl. No.: 525,558

[22] Filed: May 18, 1990

Related U.S. Application Data

[63] Continuation-in-part of Ser. No. 320,725, Mar. 8, 1989, Pat. No. 4,963,236.

[51] Int. Cl.$^5$ .................................................. G01N 27/26
[52] U.S. Cl. .............................. 204/182.9; 204/183.2; 204/299 R; 204/301
[58] Field of Search ............. 204/182.9, 183.2, 299 R, 204/301

[56] References Cited

U.S. PATENT DOCUMENTS

| | | | |
|---|---|---|---|
| 2,878,178 | 3/1959 | Bier | 204/180 |
| 3,079,318 | 2/1963 | Bier | 204/180 |
| 3,657,106 | 4/1972 | Smith | 204/301 |
| 3,677,923 | 7/1972 | Bier | 204/180 |
| 3,686,089 | 8/1972 | Korngold et al. | 204/180 |
| 3,751,356 | 8/1973 | Takeya et al. | 204/299 |
| 3,788,959 | 1/1974 | Smith | 204/180 |
| 3,901,780 | 8/1975 | Denckla | 204/180 |

(List continued on next page.)

OTHER PUBLICATIONS

Bier, M. "Forced-Flow Electrophoresis and its Biomedical Applications", Membrane Process for Industry—Proceedings of the Symposium (May 19-20, 1966), pp. 218-233.

Bier, M. et al., "Developments in Isoelectric Focusing," Peptides—Structure and Biological Function, Proceedings of Sixth American Peptide Symposium, 1979, pp. 79-89.

Fawcett, John S., "Continuous-Flow Isoelectric Focusing and Isotachophoresis, " Annals New York Academy of Sciences, pp. 112-126.

Fawcett, John S., "Continuous-Flow Isoelectric Focusing," Isoelectric Focusing, N. Catsimpoolas ed., Chapter 7 (1976), pp. 173-208.

Kolin, Alexander, "Isoelectric Focusing", Isoelectric Focusing, N. Catsimpoolas ed., Chapter 1 (1976), pp. 1-10.

Martin, A. J. P., et al., "New Apparatus for Isoelectrtic Focusing," Journal of Chromatography, vol. 159 (1978), pp. 101-110.

Nagabhushan, T. L. et al., "Application of recycling isoelectric focusing for purification of recombinant human leukocyte interferons," Electrophoresis 7 (1986), pp. 552-557.

(List continued on next page.)

Primary Examiner—John Niebling
Assistant Examiner—David G. Ryser
Attorney, Agent, or Firm—Workman Nydegger Jensen

[57] ABSTRACT

The present invention includes novel isoelectric focusing cells and methods for isoelectric focusing of amphoteric substances within fluids containing carrier ampholytes which inhibit the phenomena known as spiking or acid notching. The apparatus includes a barrier separating the electrode compartments from the focusing cell compartments which minimizes hydrogen and hydroxyl ions contained in electrolyte solution within the electrode chambers from passing into the focusing cell passageways. The currently preferred barrier is a bipolar membrane; however, the combination of anion and cation selective membranes is also effective. Such a barrier enables very narrow pH gradients to be established and maintained, thereby permitting high resolution separations of amphoteric biological substances.

26 Claims, 12 Drawing Sheets

U.S. PATENT DOCUMENTS

| | | | |
|---|---|---|---|
| 3,915,839 | 10/1975 | Rilbe et al. | 204/299 |
| 3,919,065 | 11/1975 | Heden | 204/180 |
| 3,951,777 | 4/1976 | Denckla | 204/299 |
| 3,962,058 | 6/1976 | Denckla | 204/180 |
| 3,972,791 | 8/1976 | Stern | 204/180 |
| 3,989,613 | 11/1976 | Gritzner | 204/180 |
| 4,040,940 | 8/1977 | Bier | 204/299 |
| 4,043,896 | 8/1977 | Ahlgren | 204/301 |
| 4,088,561 | 5/1978 | Anderson | 204/299 |
| 4,130,470 | 12/1978 | Rosengren et al. | 204/180 |
| 4,217,193 | 8/1980 | Rilbe | 204/180 |
| 4,234,404 | 11/1980 | Satoh | 204/299 |
| 4,243,507 | 1/1981 | Martin et al. | 204/301 |
| 4,289,596 | 9/1981 | Satoh | 204/180 |
| 4,362,612 | 12/1982 | Bier | 204/299 R |
| 4,385,974 | 5/1983 | Shevitz | 204/180 |
| 4,396,477 | 8/1983 | Jain | 204/180 |
| 4,401,538 | 8/1983 | Hausfeld | 204/180 |
| 4,416,761 | 11/1983 | Brown et al. | 294/299 |
| 4,441,978 | 4/1984 | Jain | 204/301 |
| 4,484,141 | 11/1984 | Cook et al. | 324/464 |
| 4,495,279 | 1/1985 | Kapetsky et al. | 435/6 |
| 4,533,447 | 8/1985 | Meldon | 204/181.4 |
| 4,588,492 | 5/1986 | Bier | 204/301 |
| 4,670,119 | 6/1987 | Hurd | 204/183.2 |
| 4,673,483 | 6/1987 | Mandle | 204/301 |
| 4,963,236 | 10/1990 | Rodkey et al. | 204/299 R |

OTHER PUBLICATIONS

Righetti, P. G. et al., "Theory and Fundamental Aspects of Isoelectric Focusing," Isoelectric Focusing, Chapter 1 (1976), pp. 341-376.

Rilbe, Harry, "Theoretical Aspects of Steady-State Isoelectric Focusing," Isoelectric Focusing, N. Catsimpoolas ed., Chapter 2 (1976), pp. 13-52.

Vesterberg, Olof, "The Carrier Ampholytes," Isoelectric Focusing, N. Catsimpoolas ed., Chapter 3 (1976), pp. 53-76.

APPARATUS AND METHODS FOR ISOELECTRIC FOCUSING OF AMPHOTERIC SUBSTANCES INCORPORATING ION SELECTIVE MEMBRANES IN ELECTRODE CHAMBERS

RELATED APPLICATION

This application is a continuation-in-part of copending patent application Ser. No. 07/320,725, filed Mar. 8, 1989, now U.S. Pat. No. 4,963,236 in the names of L. Scott Rodkey, Ph.D. and G. David Huff and entitled "APPARATUS AND METHODS FOR ISOELECTRIC FOCUSING," which is incorporated herein by specific reference.

BACKGROUND

1. The Field of the Invention

The present invention relates to methods and apparatus for the isoelectric focusing of amphoteric substances. More particularly, the present invention increases the resolution and separation characteristics of amphoteric biological substances by utilizing a barrier between the electrode compartments and the focusing cell compartments which has the properties of a bipolar selective membrane.

2. The Background of the Invention

Numerous areas of modern biology and genetic engineering depend on the availability of large quantities of high purity proteins. Currently available methods of protein purification include many kinds of chromatographic and electrophoretic techniques. Among these techniques, isoelectric focusing (hereinafter "IEF") has many attractive features.

The principle of IEF is based on the fact that certain biological materials (such as proteins, peptides, nucleic acids, and viruses) and even some living cells are amphoteric in nature—i.e., they are positively charged in an acidic media and negatively charged in a basic media. At a particular pH value, called the isoelectric point (hereinafter "pI"), these biomaterials will have a zero net charge.

Being charged in a pH gradient, the biomaterials migrate under the influence of an electric field until they reach the pH of their isoelectric point. At the isoelectric point, by virtue of their zero net charge, the biomaterials are not influenced by the electric field. Diffusion of "focused" biomaterials away from their pI will cause them to once again become charged, whereby they will electrophoretically migrate back to their pI. Thus, the biomaterials focus into narrow zones (defined by the pH of the medium and the electric field applied) from which the biomaterials can be selectively separated.

In one known method of isoelectric focusing, the pH gradient is established by the introduction of carrier ampholytes into the electric field. "Carrier ampholytes" are defined as ampholytes of relatively low molecular weight having conductance as well as buffer capacity, in the isoelectric state. Mixtures of synthetic polyaminopolycarboxylic acids have been used as carrier ampholytes.

In order to establish suitable pH gradients for IEF, it is necessary to have access to a great number of carrier ampholytes with isoelectric points well distributed along the pH scale. A commercial mixture of such amphoteric substances (called "Ampholine") is available from LKB Produkter AB, a Swedish Company. Ampholine is thought to be principally composed of polyaminopolycarboxylic acid molecules made by reacting polyamines with acrylic acid.

By manipulating the pH range of the carrier ampholytes, isoelectric focusing has the potential for high resolving power However, the potential of isoelectric focusing as a means for separating amphoteric substances has not been realized because of the time necessary and the quality of separation of prior art processes.

Since acids are attracted to the anode of the electric field and bases to the cathode during electrolysis, an increasing pH gradient from the anode to the cathode will develop in a convection free electrolytic conductor. The success of isoelectric focusing depends on the satisfaction of three conditions: (1) that the pH gradient is stable in time; (2) that an electrolyte deficit does not develop within the field, thereby tending to quench the current and/or give rise to local overheating; and (3) that the pH gradient—d(pH)/dx—has a low value in the pH region of interest in the actual separation.

Isoelectric focusing is most often practiced in small-scale batch instruments where the fluid is stabilized by either gels or density gradients established by a nonmigrating solute such as sucrose. The capacity of such instruments for product separation is generally limited by the cross-sectional area of the apparatus. Because the apparatus cross-section is limited by the need to dissipate the heat generated by the electric field, larger scale preparative work has been proposed using continuous flow and recycling techniques.

One known technique which comes close to combining high resolution with large quantitative capacity is the recycling isoelectric focusing method disclosed in U.S. Letters Pat. No. 4,204,929 and No. 4,362,612.

Currently known recycling isoelectric focusing (hereinafter "RIEF") techniques involve dividing a fluid containing carrier ampholytes into a plurality of reservoirs and passing the contents of the reservoirs through an isoelectric focusing cell. The isoelectric focusing cell separates the fluids from adjacent reservoirs with ion non-separates selective permeable membranes which allow interchange of fluid constituents from channel to channel, but which inhibit bulk fluid flow. Electrodes establish an electrical potential transverse to the fluid flow thereby creating a pH gradient between successive channels.

The fluid from each reservoir exiting the isoelectric focusing cell is pumped to the reservoir which feeds the isoelectric focusing cell. A heat exchanger cools the fluid within the reservoirs. As the fluid is pumped into the top of the reservoir, the fluid is directed from the bottom of the reservoir back into the isoelectric focusing cell.

One problem with this technique is the continual remixing of purified materials with semi-purified or crude starting materials. Another serious drawback with the current RIEF techniques is dissipating the joule heat generated during the isoeleotric focusing process. Solutions to these problems are disclosed in copending U.S. patent application Ser. No. 07/320,725 in the name of the inventors hereof which has been incorporated by reference.

The use of dilute acids and bases for electrolyte solutions in the electrode chambers has been standard practice for virtually all isoelectric focusing systems. Typically the solutions used are 0.1 M sodium hydroxide (pH 12.5) for the catholyte and 0.1 M phosphoric acid (pH 2.3) for the anolyte. As the ampholytes focus, the subsequent pH gradient tends to be between these two pH extremes. Even when attempting to create shallow gradients with narrow range ampholytes, the extreme ends adjacent to the electrolyte solutions buffer to the electrolyte pH. This phenomenon is known as "spiking" or "acid notching".

In many isoelectric focusing applications spiking is not a major concern. However, in applications having a small number of separation channels or other limited area of separation, it is important to reduce or eliminate spiking to achieve high resolution separations. Otherwise the spiking tends to inhibit the formation of a narrow pH gradient which is important in achieving high resolution.

From the foregoing, it will be appreciated that what is needed in the art are apparatus and methods for isoelectric focusing of amphoteric substances which inhibit spiking.

Additionally, it would be a significant advancement in the art to provide apparatus and methods for isoelectric focusing of amphoteric substances which enable narrow pH gradients to be obtained and maintained without significant spiking in the separation channels adjacent the electrodes.

It would be another advancement in the art to provide apparatus and methods for isoelectric focusing of amphoteric substances which provide high resolution separations.

Such methods and apparatus are disclosed and claimed herein.

BRIEF SUMMARY AND OBJECTS OF THE INVENTION

The present invention includes novel apparatus and methods for isoelectric focusing of amphoteric substances within fluids containing carrier ampholytes which inhibit the phenomenon known as spiking or acid notching. The apparatus preferably includes bipolar membranes to separate the electrode compartments from the focusing cell compartments. Although less preferred, anion and cation selective membranes combined may replace the single bipolar membrane. It has been found that the use of bipolar membranes to separate the electrode chambers significantly increases the resolution and separation characteristics of amphoteric biological substances.

Conventional isoelectric focusing cells use a single ion selective membrane to confine the anolyte and catholyte solutions within the electrode chambers. An anion permeable membrane used at the cathode (negatively charged electrode) repels positively charged ions. A cation permeable membrane used at the anode (positively charged electrode) repels negatively charged ions. These membranes effectively block the passage of low pH molecules into the anolyte and high pH molecules into the catholyte. The ion selective membranes alone do not prevent the passage of cations generated within the anode compartment or anions generated within the cathode compartment from entering the focusing cell.

It has been found that during the isoelectric focusing process, positively charged ions enter the focusing cell from the anolyte solution and negatively charged ions enter the focusing cell from the catholyte solution. As the length of time increases during focusing, sufficient quantities of these charged ions enter the focusing cell altering the pH near the electrodes. The negative ions are trapped in the channels of the focusing apparatus near the anode, thereby lowering the pH. Similarly, the positive ions are trapped in the channels of the focusing apparatus near the cathode, thereby raising the pH.

Experimental results suggest that if anions and cations can be prevented from passing into the focusing cell channels from the electrode chambers, spiking in the end focusing cell channels is significantly reduced. This result is achieved according to the currently preferred embodiment of the present invention by providing a barrier between the electrode chambers and the focusing cell channels which combines the characteristics of an anionic membrane and a cationic membrane. Such a barrier preferably comprises a single bipolar membrane; however, the use of an anion and a cation selective membrane in combination also accomplishes the same result. The use of a suitable bipolar membrane to separate the electrode chambers from the focusing cell chambers permits very shallow pH gradients to be obtained thereby enhancing the resolution and separation characteristics of amphoteric biological substances.

It is, therefore, a primary object of the present invention to provide apparatus and methods for isoelectric focusing of amphoteric substances which inhibit spiking or acid notching.

Another important object of the present invention is to provide apparatus and methods for isoelectric focusing of amphoteric substances which enable narrow pH gradients to be obtained and maintained without significant spiking in the separation channels adjacent the electrodes.

An additional object of the present invention is to provide apparatus and methods for isoelectric focusing of amphoteric substances which provide high resolution separations.

Other objects and advantages of the present invention will become more fully apparent from the following detailed description and appended claims taken in conjunction with the accompanying drawings, or may be learned from the practice of the invention.

DETAILED DESCRIPTION OF THE PREFERRED EMBODIMENTS

Reference is now made to the drawings wherein like parts are designated with like numerals throughout. As discussed generally above, the present invention is directed to apparatus and methods for isoelectric focusing of amphoteric substances, particularly biological materials. The apparatus of the present invention includes an isoelectric focusing cell having means for separating the electrolyte solutions from the separation channels which minimize the passage of both cations and anions into the separate channels.

For the purposes of discussion, reference will be made to a recycling isoelectric focusing apparatus. It will be appreciated that the present invention is not limited to a recycling isoelectric focusing apparatus and may be advantageously applied to conventional isoelectric focusing apparatus. However, given the objective of maximizing separation of amphoteric substances, It is currently believed that the best mode of maximizing separation is to use a liquid phase isoelectric focusing apparatus, such as the one described in copending U.S. patent application Ser. No. 07/320,725, in combination with the principles of the present invention.

A. Liquid Phase Isoelectric Focusing Apparatus

Figure 1:
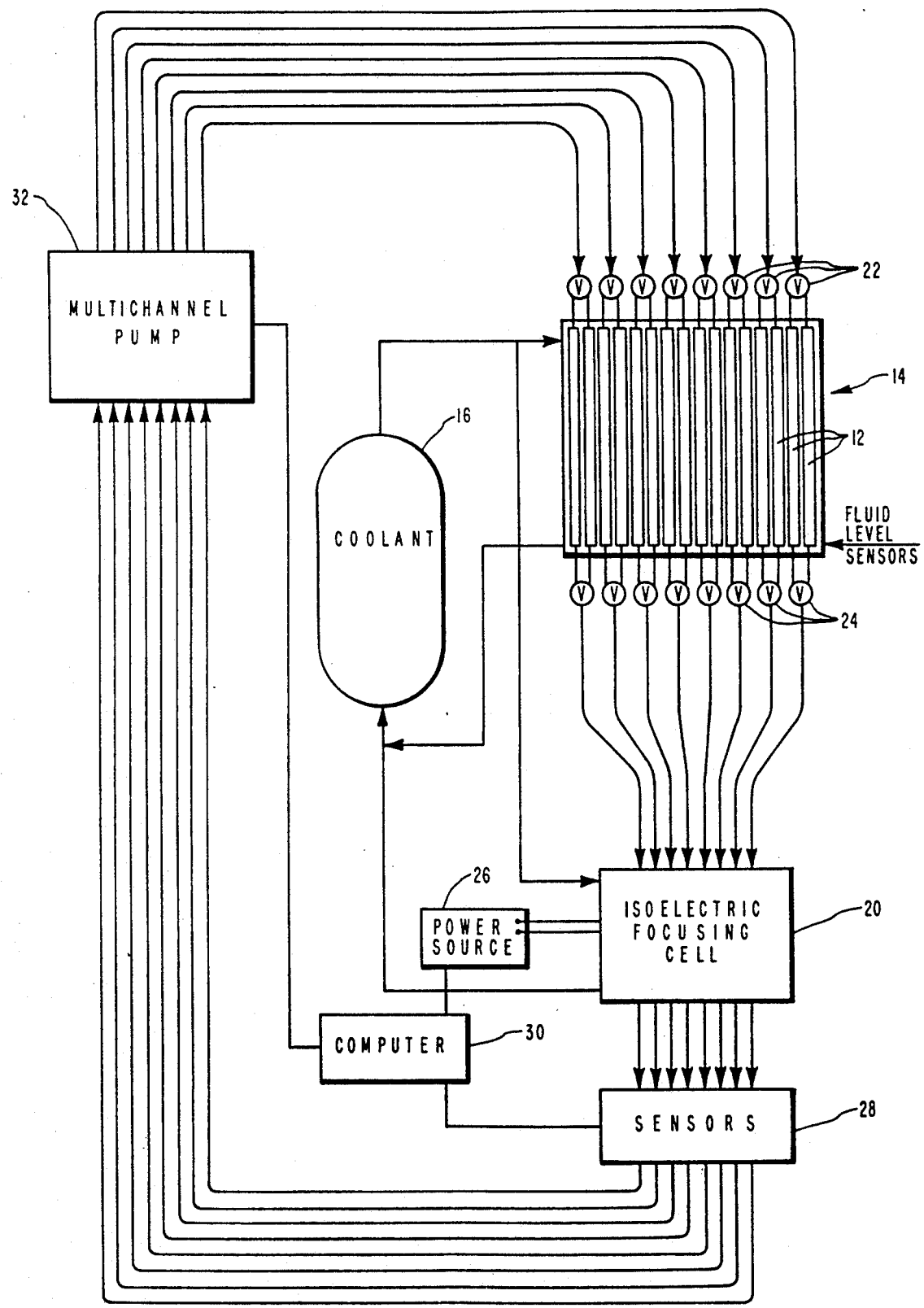
FIG. 1 is a schematic diagram of the recycling isoelectric focusing apparatus within the scope of the present invention.
Figure 2:
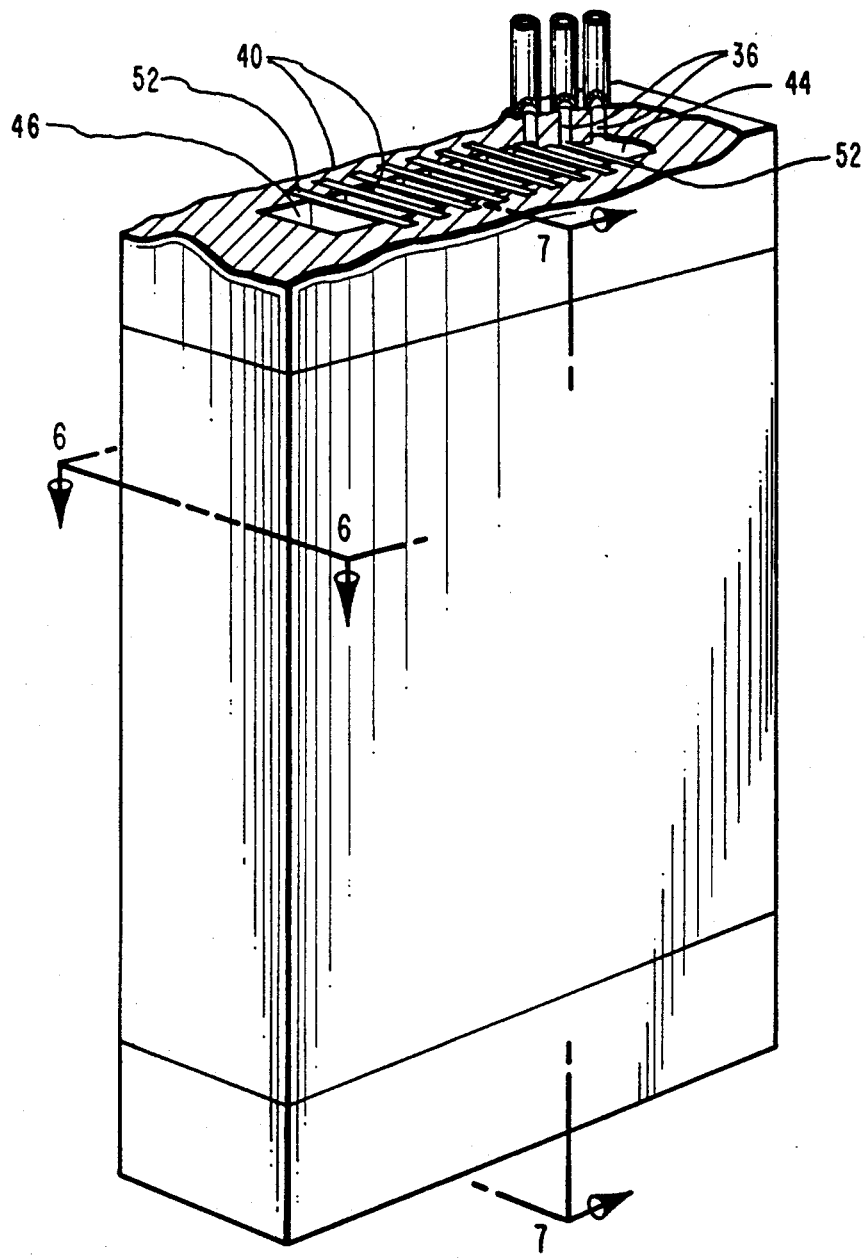
FIG. 2 is a partial cut-away perspective view of an isoelectric focusing cell within the scope of the present invention.

Referring first to FIG. 1, a schematic view of an overall isoelectric focusing apparatus, such as the one described in copending U.S. patent application Ser. No. 07/320,725, is illustrated. An important concept of the isoelectric focusing apparatus shown in FIG. 1 is eliminating the mixing of semipurified and crude amphoteric substances during recycling. Mixing is avoided by preferably using an alternating or dual reservoir system. Thus, a plurality of reservoirs 12, arranged in pairs, are provided. Reservoirs 12 are located in a reservoir housing 14 which is coupled to a coolant source 16 for cooling the reservoirs within reservoir housing 14.

One reservoir of each reservoir pair supplies the sample fluid to isoelectric focusing cell 20 and the other reservoir of each reservoir pair receives the fluid that has passed through isoelectric focusing cell 20. After the supply reservoir empties, fluid flow into isoelectric focusing cell 20 is automatically diverted from the supply reservoir to the receiving reservoir. Fluid flow from the isoelectric focusing cell into the receiving reservoir is then diverted into the supply reservoir. Thus, fluid flow into and out of each reservoir is automatically alternated after each cycle through the isoelectric focusing cell.

Fluid flow is preferably alternated into and out of each reservoir pair through use of reservoir inlet valves 22 and reservoir outlet valves 24. The reservoir inlet and outlet valves preferably operate in response to the fluid level within the reservoir supplying fluid to the isoelectric focusing cell. When the reservoir empties, as measured by fluid level sensors, the corresponding reservoir outlet valve automatically engages to stop fluid flow from the empty reservoir and to start fluid flow from the full reservoir. After appropriate time delay, the reservoir inlet valve engages to stop fluid flow into the full reservoir and to start fluid flow into the empty reservoir.

The isoelectric focusing apparatus shown in FIG. 1 may also provide direct cooling of the isoelectric focusing cell 20 by coolant 16. In this way, heat generated by the isoelectric focusing cell is directly removed. The heat is generated by an electric potential across the isoelectric focusing cell. Power source 26 coupled to isoelectric focusing cell 20 provides the necessary electric potential. Direct cooling of the isoelectric focusing cell permits greater power input to the focusing cell which results in rapid focusing and separation of the fluid sample.

Sensors 28 may be provided to measure the temperature, pH or sample concentration in one or more of the outlet channels. Sensors 28 are preferably coupled to computer 30 which may control, monitor, and record the isoelectric focusing process. In addition, the power input to isoelectric focusing cell 20 from power source 26 may be monitored and adjusted by computer 30 in response to the temperature of the fluid within the focusing cell to maximize the efficiency of the focusing process. Similarly, multichannel pump 32 may be controlled by the computer to balance fluid flow through the apparatus with power input and fluid sample separation. Multichannel pump 32 returns the sample fluid exiting isoelectric focusing cell 20 to reservoirs 12.

B. Isoelectric Focusing Cell

Referring now to FIGS. 2–7, one possible isoelectric focusing cell 20 within the scope of the present invention is illustrated. Isoelectric focusing cell 20 includes a plurality of inlet ports 36 and a plurality of corresponding outlet ports 38. Isoelectric focusing cell 20 preferably includes means for separating the fluid flow into a plurality of focusing cell passageways 40. Each focusing cell passageway is coupled to a corresponding inlet port 36 and outlet port 38.

Electrodes 42 are located within the isoelectric focusing cell in order to create an electric potential across focusing cell passageways 40. Electrodes 42 may be constructed of platinum or any other suitable electrode material used in isoelectric focusing devices.

An electrolyte solution preferably surrounds each electrode 42. The electrolyte fluids associated with the anode and cathode are generally referred to as the anolyte and catholyte fluids, respectively. The anolyte may be a dilute solution of a strong acid such as sulfuric or phosphoric acid, in the anode or positive electrode compartment 44, as is conventional for isoelectric focusing instruments. The catholyte may be a dilute solution of a strong base, such as sodium hydroxide which flows in the cathode or negative electrode compartment 46 as is conventional for isoelectric focusing instruments.

Other electrolyte solutions may also be used. For instance, narrow and stable pH gradients have been obtained using glycine, potassium nitrate (KNO$_3$), and even water, as electrolyte solutions. Suitable results may be obtained by matching the anolyte and catholyte as closely as possible to the lower and upper pH of the pH gradient using 0.1 M glycine with the pH adjusted using either HCl or NaOH. However, it has been found that the choice of electrolyte solutions has little effect on the formation of stable and narrow pH gradients according to the principles of the present invention. In fact, experimental results suggest that the pH gradient formation in the present invention is strongly a function of ampholyte solution and not the electrolyte solution.

In one possible embodiment within the scope of the present invention each electrode compartment 44 and 46 is separated from focusing cell passageways 40 by both an anionic or anion selective membrane 48 and a cationic or cation selective membrane 50. The anionic and cationic membranes should preferably be ion-selective membranes of the type used in electrodialysis and ion exchange processes. Satisfactory ion-selective membranes are manufactured by Sybron Chemicals Inc., Birmingham, N.J. Typical properties of ion-selective membranes which have been found suitable are summarized in Table 1.

TABLE 1

|  | Cationic | Anionic |
| --- | --- | --- |
| Permselectivity (0.5N NaCl/1.0N NaCl) | 96% | 99% |
| Electrical Resistance (ohm-cm$^2$, AC measurement) |  |  |
| 0.1N NaCl | 14 | 17 |
| 1.0N NaCl | 6 | 8 |
| Mullen Burst Strength (minimum psi.) | 200 | 200 |
| Thermally Stable | to 80° C. | to 80° C. |
| Chemically Stable |  |  |
| H$_2$SO$_4$ and HCl | to 35% | to 35% |
| NaOH | to 50% | to 5% |
| Salt | all conc. | all conc. |
| Oxidizing solutions | to 16% HIO$_4$ 5% NaOI 150 mg Cl$_2$ | to 16% HIO$_4$ 5% NaOI |
| Water Permeability (ml/hr/ft$^2$/5 psi) | <30 | <50 |
| Membrane Thickness (mils) | 16 | 16 |

Figure 3:
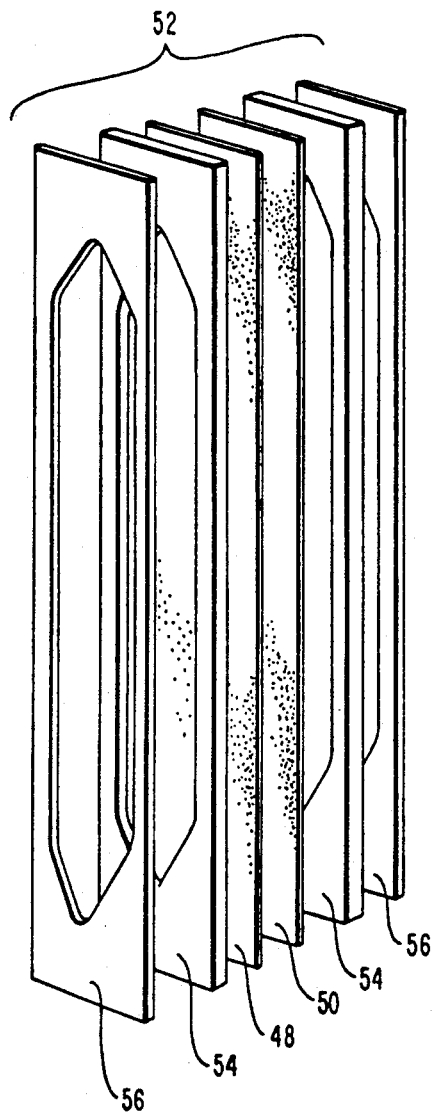
FIG. 3 is an exploded perspective view of an electrode separator having dual ion-selective membranes within the scope of the present invention.
Figure 4:
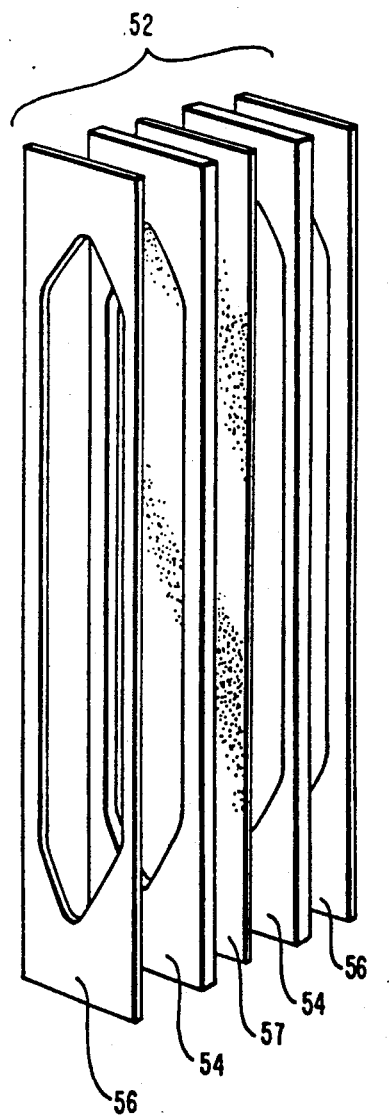
FIG. 4 is an exploded perspective view of an electrode separator having bipolar membrane within the scope of the present invention.
Figure 5:
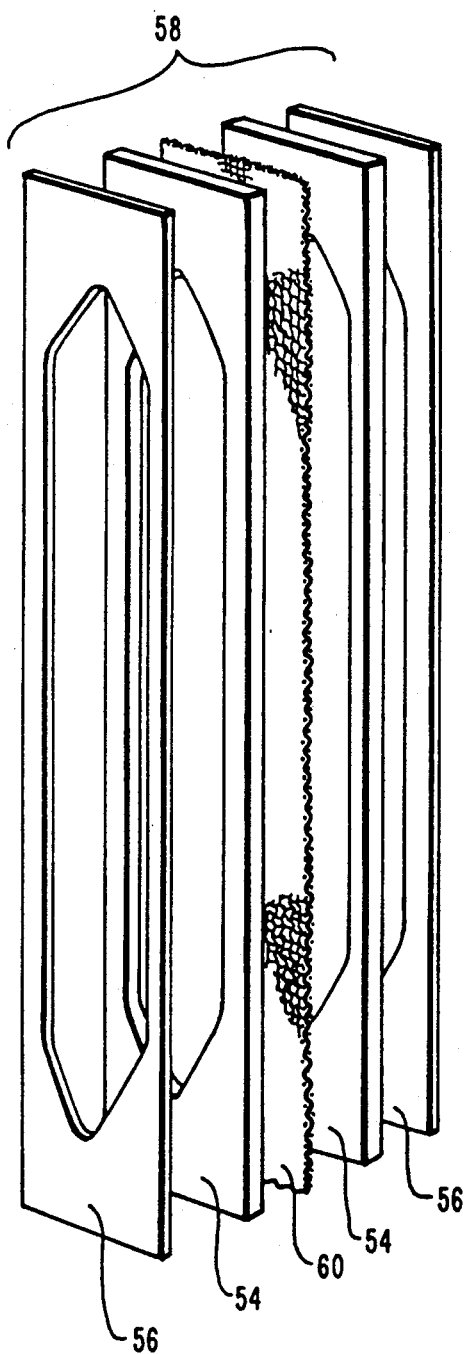
FIG. 5 is an exploded perspective view of a cell separator within the scope of the present invention.
Figure 6:
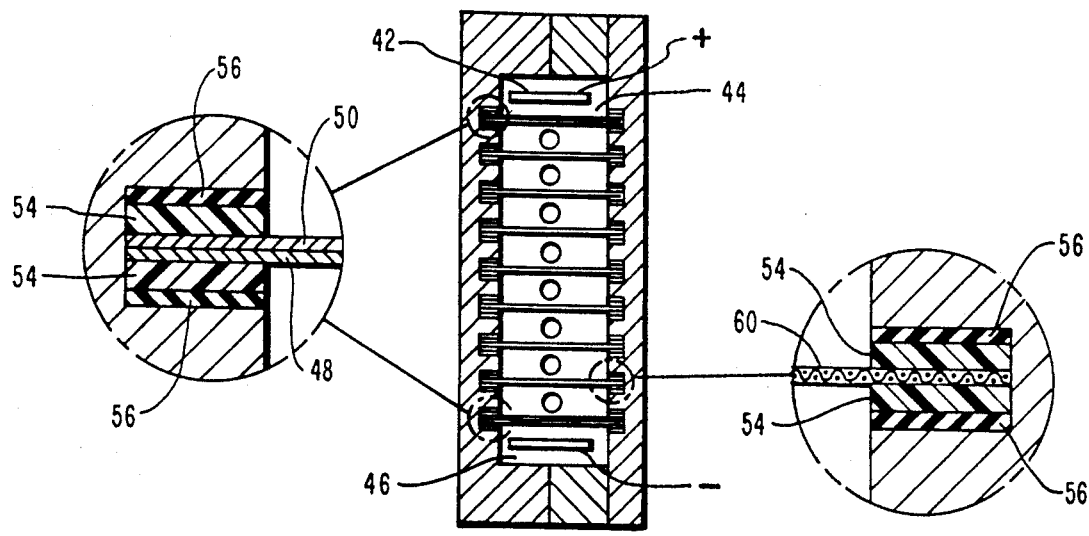
FIG. 6 is a horizontal cross-sectional view of the isoelectric focusing cell of FIG. 2 taken along line 6—6 of FIG. 2.
Figure 7:
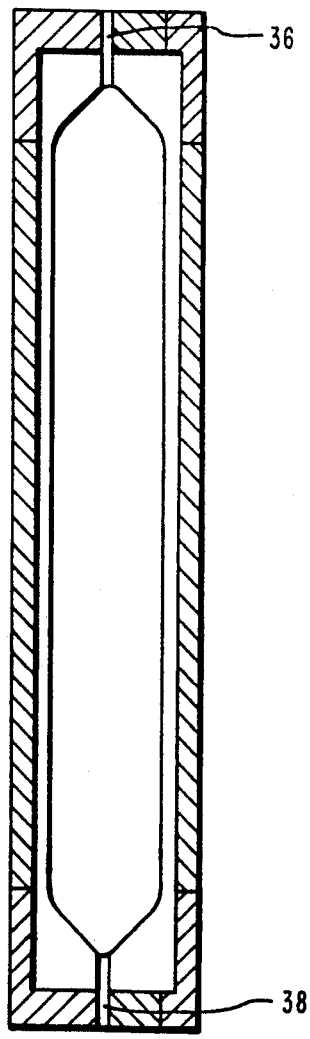
FIG. 7 is a vertical cross-sectional view of the isoelectric focusing cell of FIG. 2 taken along line 7—7 of FIG. 2.

The anionic and cationic membranes preferably form part of an electrode separator 52, shown best in FIGS. 3, 4, and 6. In FIGS. 3 and 6, each electrode separator includes an anionic membrane 48 and a cationic membrane 50 sandwiched between two supports 54 and two gaskets 56. In FIG. 4, the electrode separator includes a single bipolar membrane 57 sandwiched between two supports 54 and two gaskets 56. The bipolar membrane 57 possesses characteristics of both anionic and cationic selective membranes 48 and 50, respectively.

In fact, a single bipolar membrane is currently preferred over the use of dual anionic and cationic membranes. In some cases using dual anionic and cationic membranes fluid becomes trapped between the membranes. Without the capacity to circulate and cool the trapped fluid, the fluid may overheat and damage the membranes or otherwise limit the efficiency of the isoelectric focusing device. Thus, to avoid the possibility of fluid becoming trapped between the anionic and cationic membranes, use of a single bipolar membrane is currently preferred. The typical physical properties of one suitable bipolar membrane used within the scope of the present invention is approximated by the combined properties of the anionic and cationic membranes identified in Table 1.

Supports 54 are generally of a material providing adequate support while being neutral in the electrical field and nonreactive with the electrolyte solutions and with the ampholytes. Supports 54 may suitably be constructed of ultra high molecular weight polyethylene. Gaskets 56 are preferably constructed of an elastic, nonreactive material such as neoprene. Other suitable materials with sealing capacity and neutrality, such as VITON ® polymers manufactured by DuPont, may also be satisfactory under certain conditions.

Isoelectric focusing cell passageways 40 are preferably separated by a plurality of cell separators 58. As shown more clearly in FIG. 5 and FIG. 6, each cell separator includes five components sandwiched together. Each cell separator includes a screen 60, two supports 54, and two gaskets 56.

Screen 60 is preferably constructed of a biocompatible mesh material such as nylon or teflon. It has been found that a pore size as large as 100 microns is suitable for most amphoteric substances separated by isoelectric focusing.

Biocompatibility is an important characteristic for all components of the isoelectric focusing apparatus within the scope of the present invention. The term biocompatible material used in this specification includes materials which will not denature sensitive proteins being separated or react with or contaminate the proteins.

Generally, the amphoteric substances separated by isoelectric focusing have a molecular weight less than about 500,000. Higher molecular weight substances may be used, provided they remain in solution long enough to be separated effectively by isoelectric focusing. As a general rule, the larger the amphoteric substance, the lower the solubility. In many cases solubility can be increased by using suitable solubilizing agents. Thus, the limiting factor in determining suitable amphoteric substances is often the molecular weight of the amphoteric substance, and not the pore size of screen 60.

It is currently preferred that the solubilizing agents be nonionic and not chemically reactive with either the protein or the ampholytes. Urea, for instance, at 1–5 Molar concentration has been used to enhance solubility without denaturing the proteins being separated. Nonionic detergents such as Nonidet P-40 and low concentrations (5%–10%) butanol have been used successfully. Basically, any nonionic substance can be added to the amphoteric substances to enhance solubility. For example, glycerol could be added to enhance the solubility of hydrophobic molecules.

Figure 8:
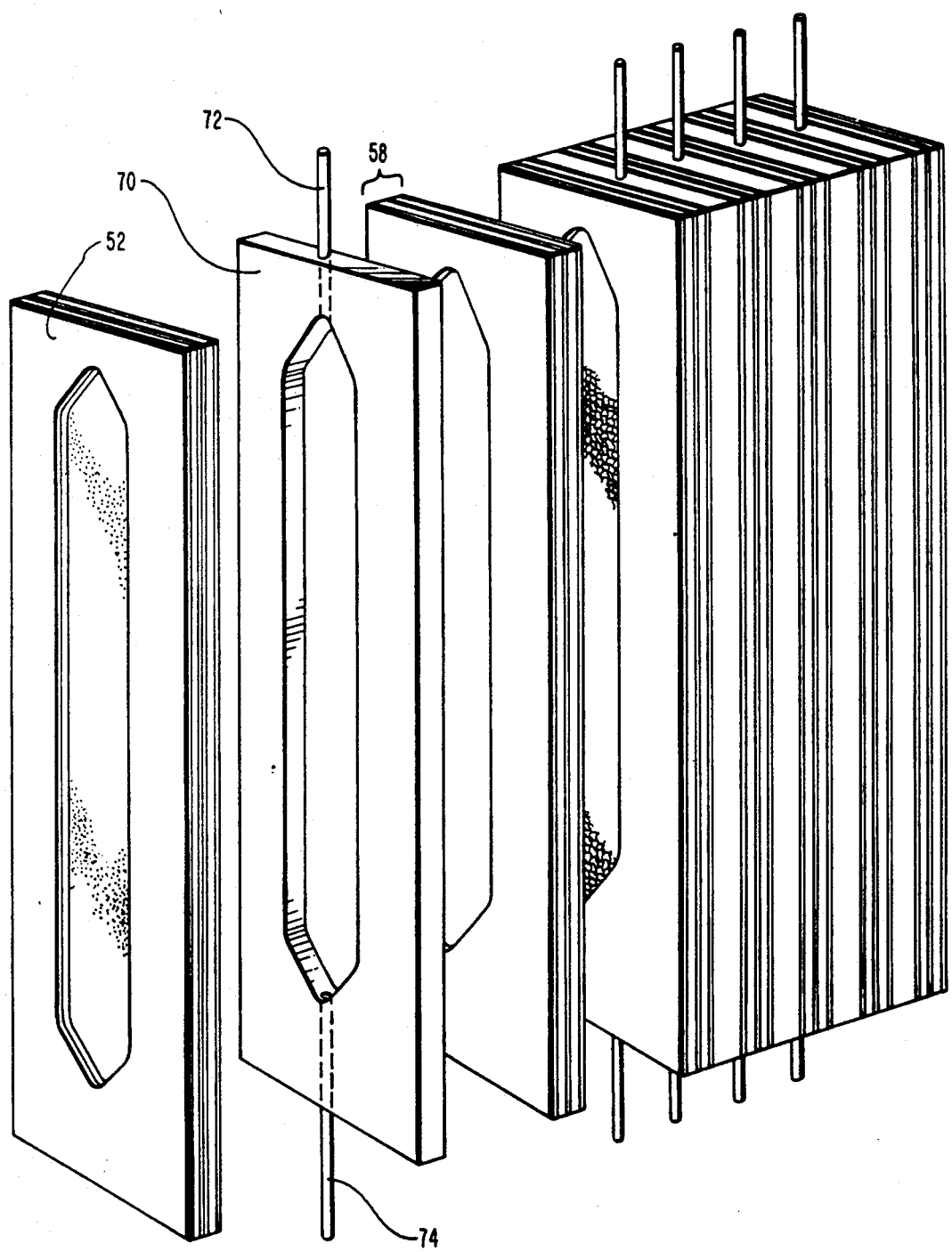
FIG. 8 is an exploded perspective view of another isoelectric focusing cell within the scope of the present invention.

Another isoelectric focusing cell within the scope of the present invention is illustrated in FIG. 8. The isoelectric focusing cell of FIG. 8 may be adjusted to increase or decrease the number of focusing cell passageways in the device. As shown in FIG. 8, individual focusing cell elements 70 may be positioned between alternating focusing cell separators 58 (illustrated in FIG. 4). Electrode separators 52 (illustrative embodiments of which are shown in FIGS. 3 and 4) may be used to separate the electrode compartments from the individual focusing cell elements 70.

Fluid flows into each focusing cell element through an inlet port 72 and exits each focusing cell element through a corresponding outlet port 74. Utilizing the embodiment illustrated in FIG. 8, it is possible to customize the isoelectric focusing cell into the ideal number of focusing cell passageways required to effect the desired separation. A larger number of focusing cell passageways would be useful to separate two or more proteins which are very close to one another in pI (i.e.. pI of 6.4 and pI of 6.8). Thus, in a narrow pH gradient made with narrow range ampholytes, a cell with many passageways would help separate the two proteins more efficiently.

Fewer focusing cell passageways would be needed to separate two proteins which have very different pI (i.e., pI of 4 and pI of 8). These would be separated in a wide range gradient and only 3-4 passageways might be necessary for effective separation.

All materials used to construct those portions of the isoelectric focusing apparatus within the scope of the present invention which contact the fluid sample are preferably constructed of biocompatible materials. Biocompatible materials are preferred because most amphoteric substances to be separated are biomaterials such as proteins, peptides, nucleic acids, viruses, and even some living cells. Thus, it is important that all surfaces which contact the amphoteric substances are inert with respect to the amphoteric substances.

In one possible mode of operation using the system described in conjunction with FIG. 1, the solutions are gravity fed from each reservoir pair within reservoir housing 14 to isoelectric focusing cell 20. The isoelectric focusing cell is preferably vertically oriented, i.e., focusing cell separators 58 are in the vertical direction.

In another possible mode of operation, the fluid is drawn through the isoelectric focusing cell against gravity due to the suction forces of the pump. It has been observed that forcing the fluid through the focusing cell with pressure from the pump results in a more unstable flow pattern than when fluid is drawn through the focusing cell with suction forces from the pump.

The selected buffer solution containing carrier ampholytes suitable for establishment of a stable pH gradient is loaded into one of the two reservoirs of each reservoir pair. A commercially available carrier ampholyte solution is suitable, while appreciating that some give much better results than others. An electrolyte solution is loaded into those reservoirs coupled to electrode compartments 44 and 46. These electrode rinses are allowed to flow upward through isoelectric focusing cell 20 to permit venting of gases generated by electrolysis.

After equilibration of fluid flow and temperature, electric power is applied from power source 26. Typically, a gradient of about 200 volts to about 250 volts at a constant current is sufficient to cause rapid equilibration. Power input into the focusing cell is maintained relatively constant throughout the separation process. Typical power input is in the range from about 30 watts to about 60 watts. It has been found that the width of the pH gradient significantly affects the time to establish equilibrium. Narrow pH gradients may take longer to form than wide pH gradients.

As focusing of the carrier ampholytes occurs, the voltage may be increased up to about 500 to about 600 volts in order to maintain current flow. The maximum power input is limited by the allowable temperature rise in the apparatus due to Joule heating. For this reason, continuous or periodic temperature monitoring is preferred. Typically, a reservoir temperature of 4° C. is maintained. The temperature may increase up to about 10° C. without causing damage to most biomaterials.

In practice, the carrier ampholyte solution is circulated through the apparatus in order to establish a relatively stable pH gradient before the sample material is added. The sample material is then preferably added only to the channel or compartment having a pH relatively close to the pI of the one protein which is desired. It is possible to add the sample material to be focused at the beginning of the operation. Nevertheless, this will cause some of the material to be exposed to extremes of pH in the compartments adjacent to the electrodes. This may damage some pH sensitive biomaterials and promote ampholyte/protein interaction.

In addition, the protein of interest might be ionically altered by exposing it to the whole ampholyte mixture. For example, a protein with acidic pI would be brought into contact with the whole ampholyte mixture if mixed in with the beginning ampholytes prior to running. Some or all of the protein of interest could then bind to some basic ampholytes, thus creating artificial heterogeneity of charge. This might cause all or part of the protein of interest to focus at a different pH than it should. When added to the reservoir containing ampholytes at or very close to the pI of the protein, it never encounters extreme pH ampholytes, thus retaining its inherent charge and pI.

It has been observed that periodic disruption of the fluid flow and of the electric current flow may improve the separation efficiency of the isoelectric focusing apparatus. Although not fully understood, it is currently believed that "dead spots" form within the focusing cell during operation. By periodically turning the apparatus "off," amphoteric substances within the dead spots is removed and circulated with the remainder of the fluid through the isoelectric focusing apparatus.

Although the optimum disruption protocol has not yet been established, it has been observed that more efficient separation is achieved by turning the power off for about 30 reversing the pump.

A series of experiments were conducted to determine the effect the pH of the electrolyte solutions had on the final pH gradient in the isoelectric focusing apparatus. These experiments were also intended to understand how to control spiking or acid notching so that high resolution separations could be more easily realized. The following examples are intended to be purely exemplary of the use of the invention and should not be considered limiting as to the scope of the present invention.

EXAMPLE 1

In this example, the effect of electrolyte solution pH on the ultimate pH gradient was determined using an eight channel isoelectric focusing device having a single anion selective membrane separating the catholyte solution from the ampholytes and a single cation selective membrane separating the anolyte solution from the ampholytes. The catholyte solution was 0.1 M sodium hydroxide having a pH of about 12.5. The anolyte solution of 0.1 M phosphoric acid having a pH of about 2.3. Narrow range ampholytes designed to produce a pH gradient from pH 7 to pH 9 were used. Upon focusing the apparatus, spiking was observed in those channels adjacent to the electrolyte solutions.

EXAMPLE 2

In this example, the effect of electrolyte solution pH on the ultimate pH gradient was determined using an eight channel isoelectric focusing device having a single anion selective membrane separating the catholyte solution from the ampholytes and a single cation selective membrane separating the anolyte solution from the ampholytes. The anolyte solution was glycine buffered to a pH of 6.0. The catholyte solution was glycine buffered to a pH of 8.0. Narrow range ampholytes designed to produce a pH gradient from pH 7 to pH 9 were used. Upon focusing the apparatus, spiking was observed in those channels adjacent to the electrolyte solutions, but to a lesser degree than that of Example 1. The results of this Example are illustrated in FIG. 9.

EXAMPLE 3

In this example, the effect of electrolyte solution pH on the ultimate pH gradient was determined using an eight channel isoelectric focusing device having both anion and cation selective membranes separating the anolyte and catholyte solutions from the ampholytes. The anolyte solution was glycine buffered to a pH of 6.0. The catholyte solution was glycine buffered to a pH of 8.0. Narrow range ampholytes designed to produce a pH gradient from pH 7 to pH 9 were used. Upon focusing the apparatus, almost no spiking was observed in those channels adjacent to the electrolyte solutions.

Figure 9:
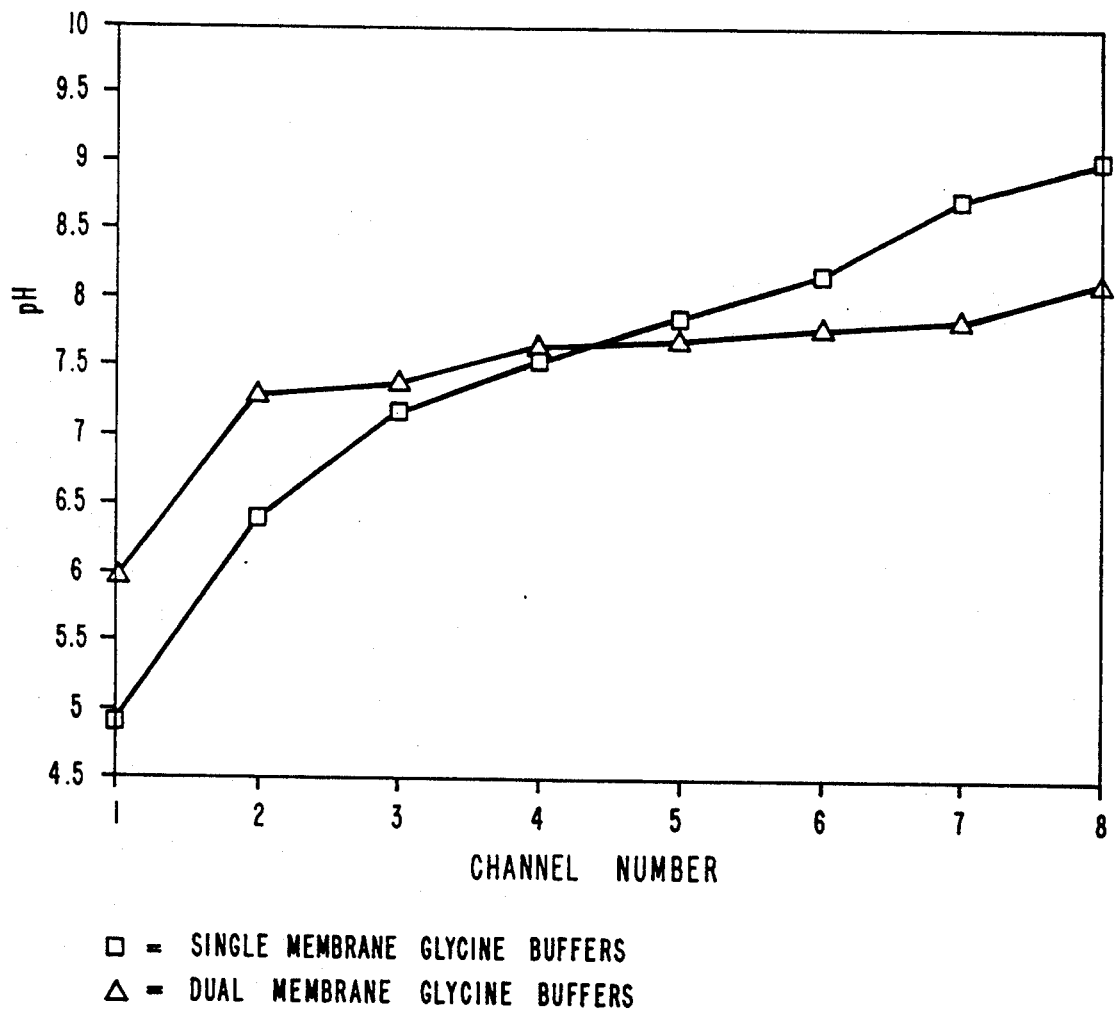
FIG. 9 is a graph of pH verses channel number illustrating the results of Examples 2 and 3.
Figure 10:
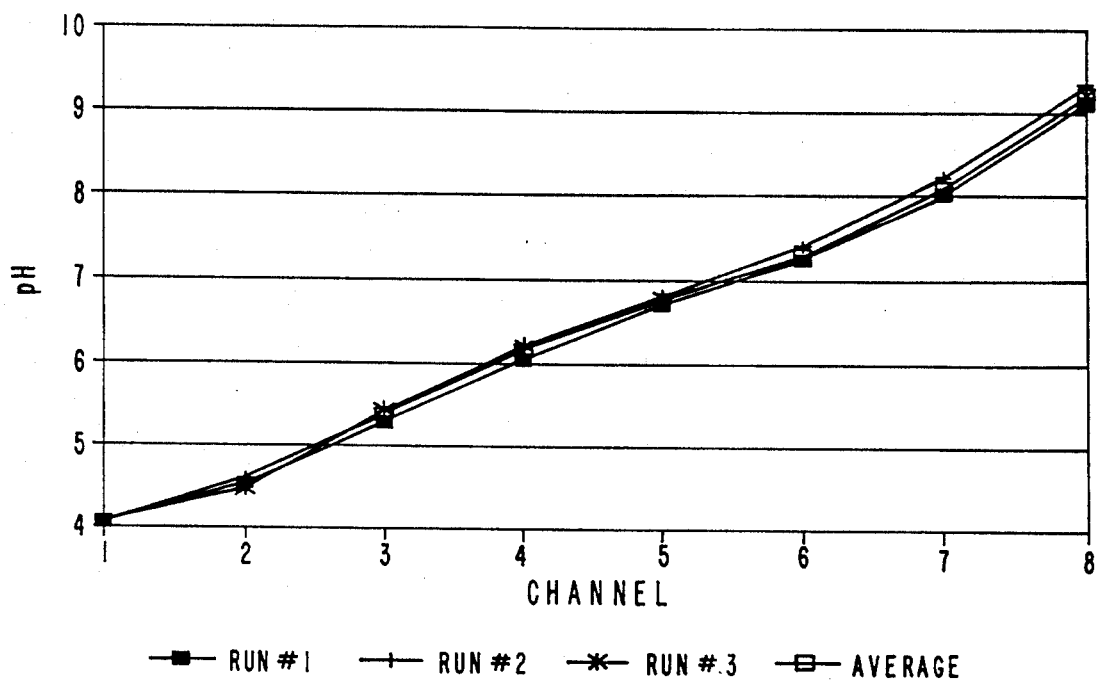
FIG. 10 is a graph of pH verses channel number illustrating the results of Example 4.
Figure 11:
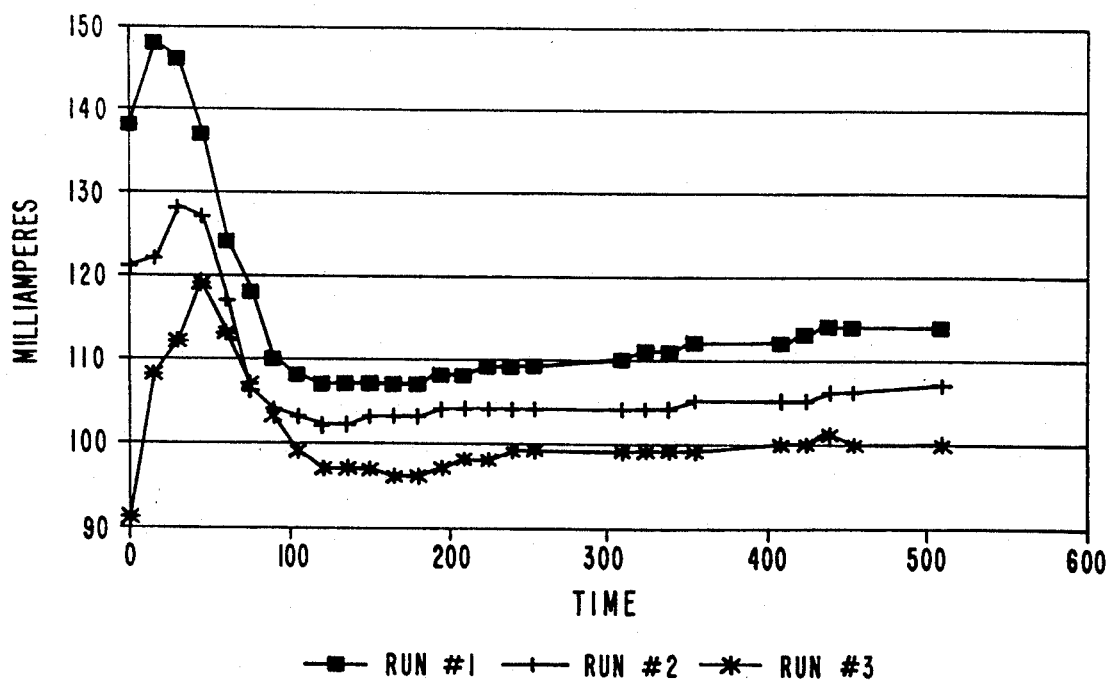
FIG. 11 is a graph of milliamperes verses time illustrating the results of Example 4.
Figure 12:
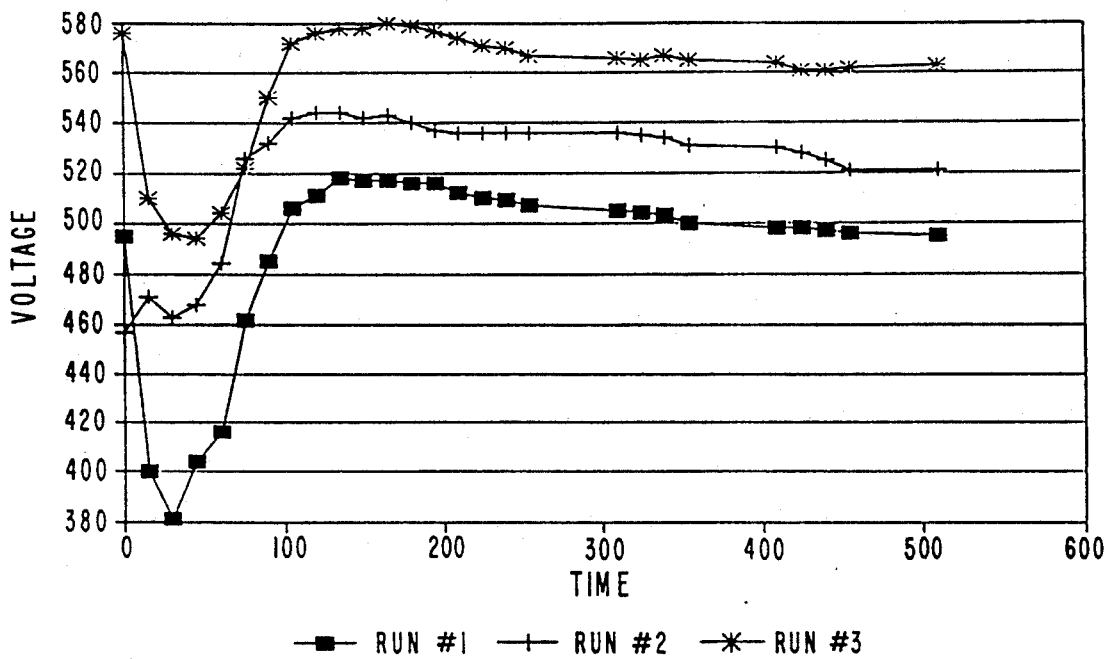
FIG. 12 is a graph of voltage verses time illustrating the results of Example 4.
Figure 13:
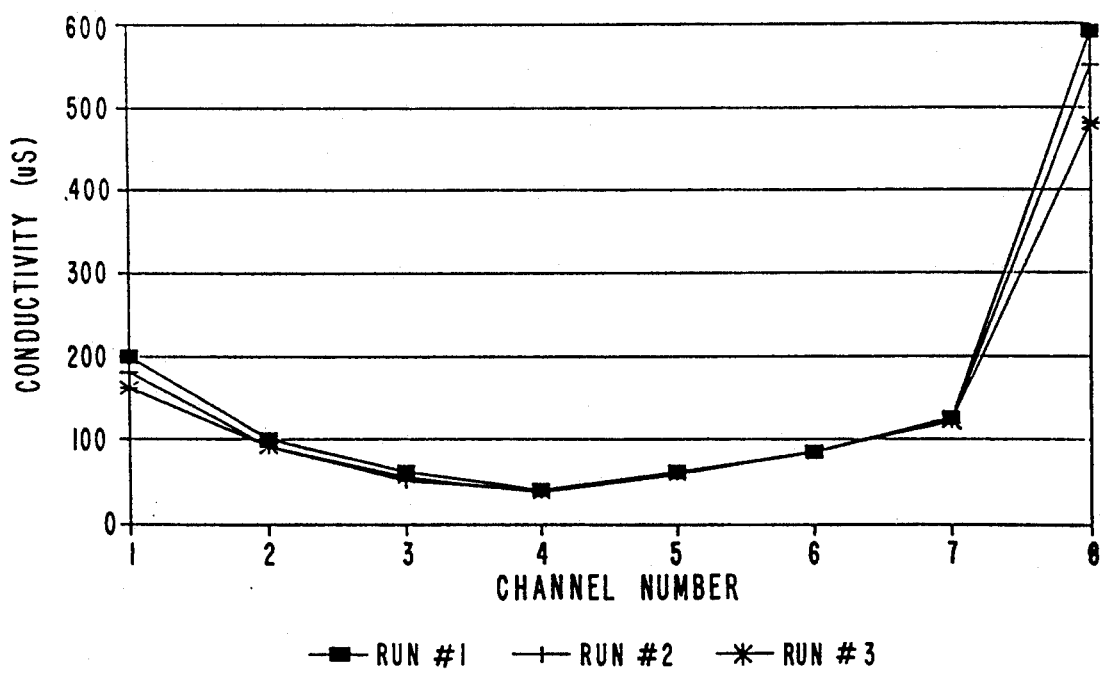
FIG. 13 is a graph of conductivity verses channel number illustrating the results of Example 4.
Figure 14:
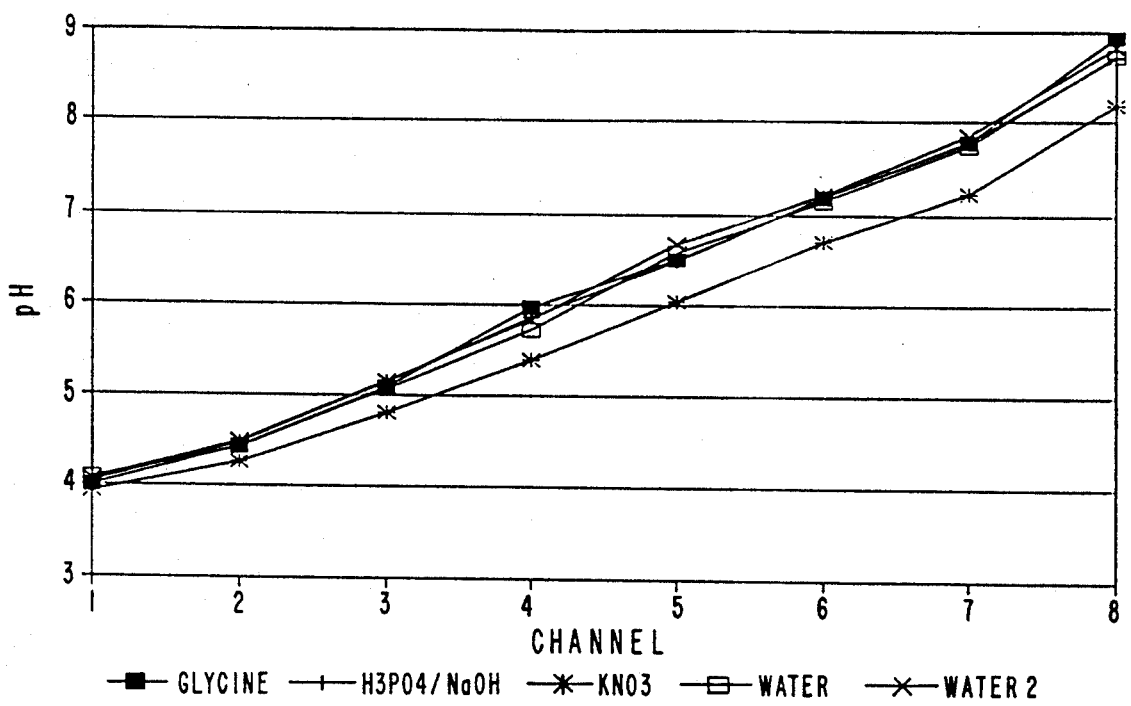
FIG. 14 is a graph of pH verses channel number illustrating the results of Example 5.
Figure 15:
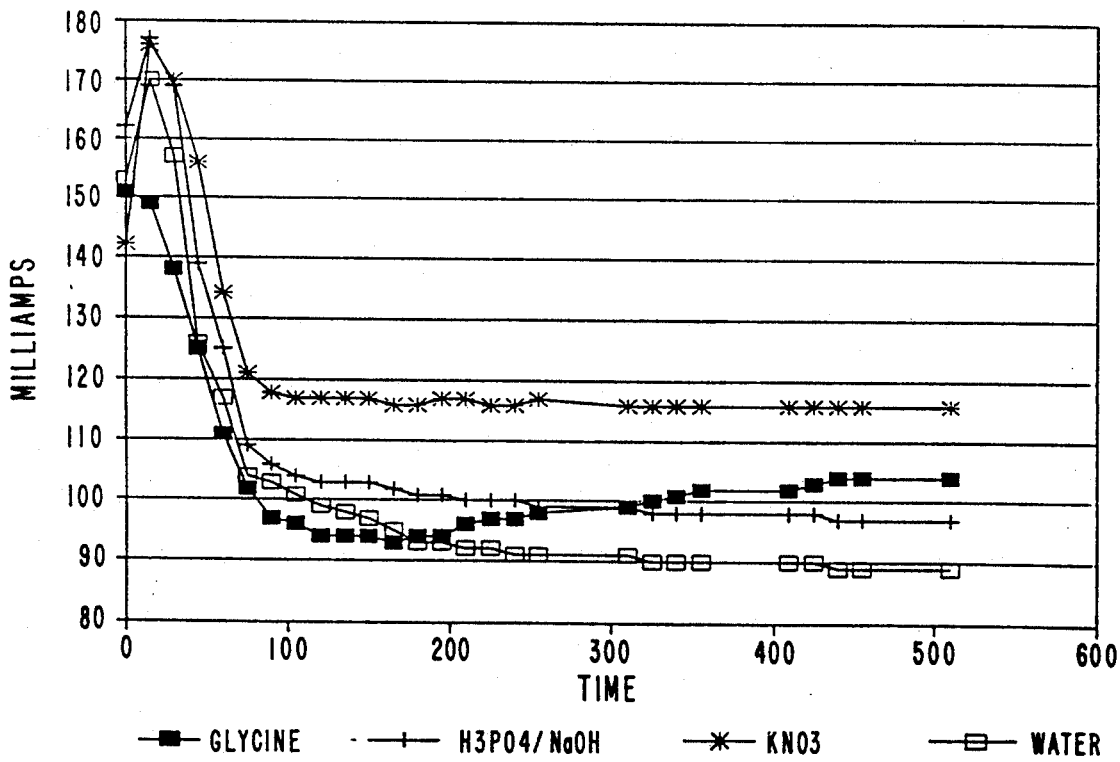
FIG. 15 is a graph of milliamperes verses time illustrating the results of Example 5.
Figure 16:
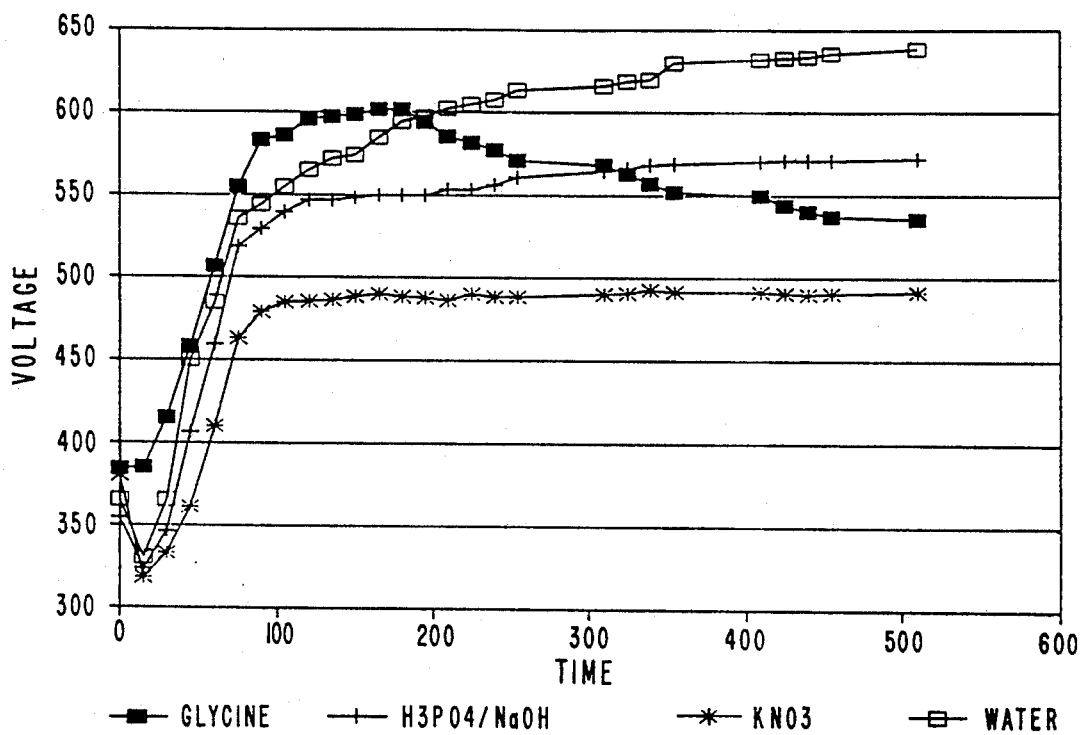
FIG. 16 is a graph of voltage verses time illustrating the results of Example 5.
Figure 17:
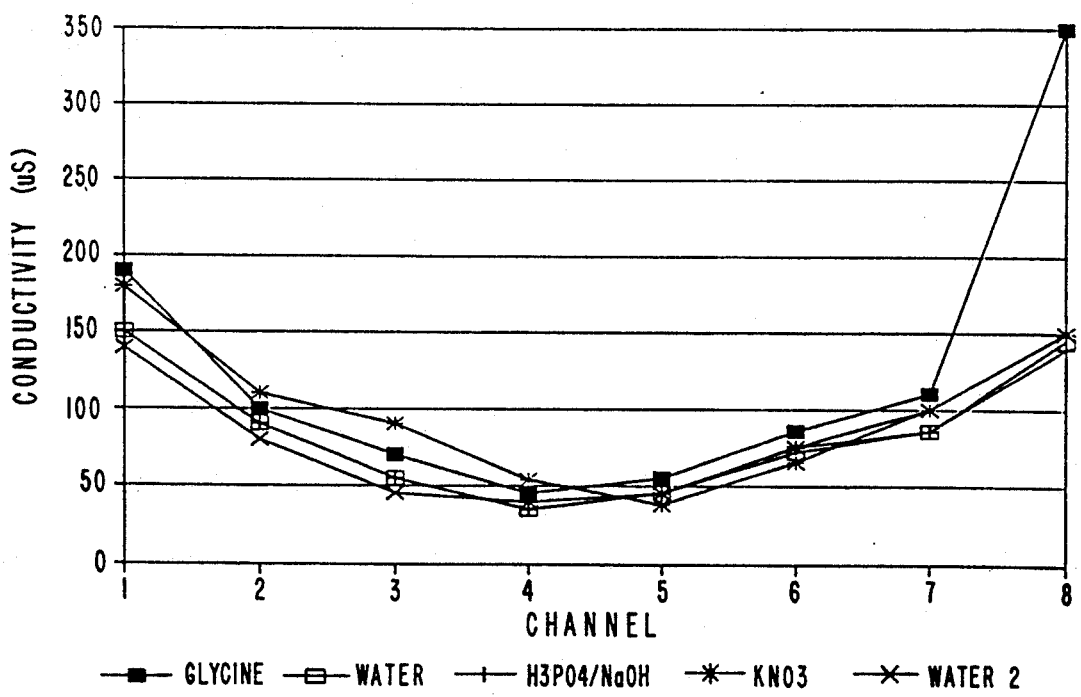
FIG. 17 is a graph of conductivity verses channel number illustrating the results of Example 5.

FIG. 9 provides a graphical comparison of the results from Examples 2 and 3. The results suggest that using a dual ion-selective membrane and appropriately buffered electrolyte solutions that very narrow pH gradients can be successfully achieved, thereby permitting high resolution separation of amphoteric substances.

EXAMPLE 4

In this example, the effect of electrolyte solution on the ultimate pH gradient was determined using an eight channel isoelectric focusing device having bipolar membranes separating the anolyte and catholyte solutions from the ampholytes. The anolyte and catholyte solutions were both 0.1 M glycine. Upon focusing the apparatus, almost no spiking was observed in those channels adjacent to the electrolyte solutions. The procedure was followed three (3) times to establish baseline operation. Repeatable pH gradients were generated when using 0.1 M unadjusted glycine. The results are shown graphically in FIGS. 10–13.

EXAMPLE 5

In this example, the effect of different electrolyte solutions on the ultimate pH gradient was determined using an eight channel isoelectric focusing device having bipolar membranes separating the anolyte and catholyte solutions from the ampholytes. The following anolyte and catholyte solutions were tested: 0.1 M glycine (anolyte and catholyte); 0.1 M $KNO_3$ (anolyte and catholyte); 0.1 M $H_3PO_4$ (anolyte)/0.1 M NaOH (catholyte); and water (anolyte and catholyte). Upon focusing the apparatus, almost no spiking was observed in those channels adjacent to the electrolyte solutions. The results are shown graphically in FIGS. 14–17.

The pH gradient and conductivity gradient from all runs using the different electrolyte solutions are virtually identical. This suggests that the pH gradient is a function of the ampholyte solution. Outside variables appear to have no substantial effect on the formation of a stable, reproducible pH gradient. The volts and milliamperes follow the same pattern, but have different end points for the different electrolyte solutions. It is currently believed that this may be attributed to the differences in conductance of the electrolytes.

EXAMPLE 6

Figure 18:
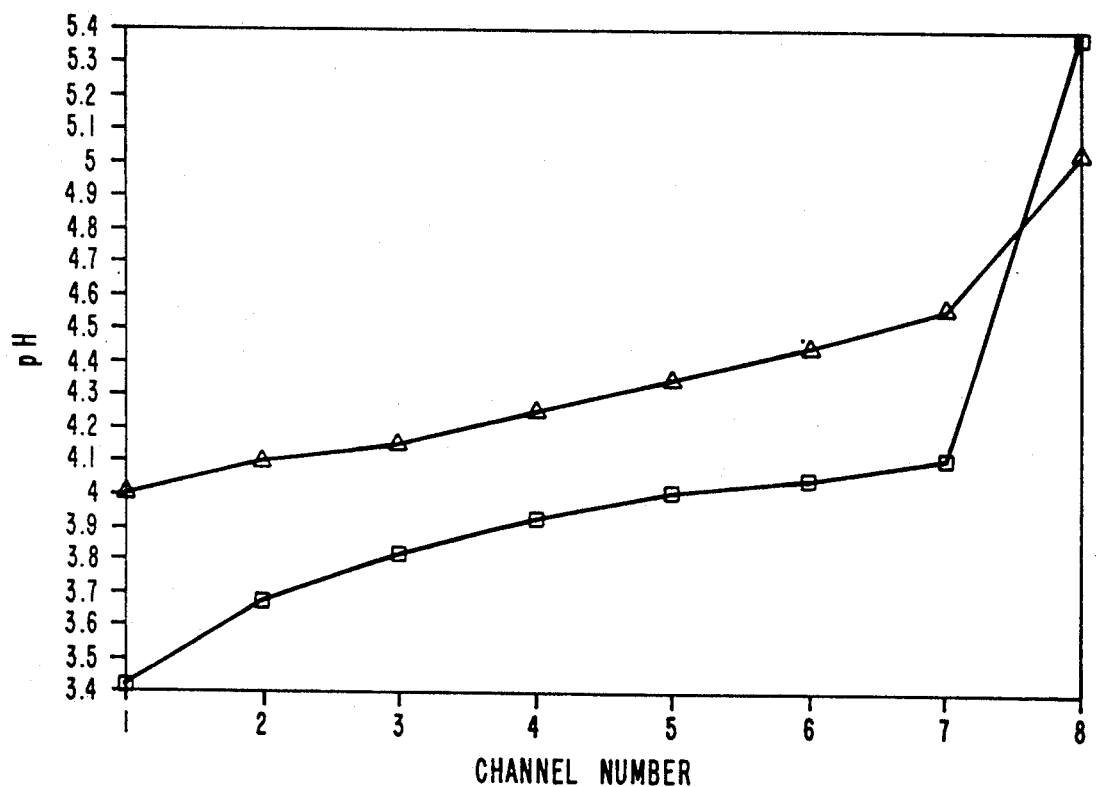
FIG. 18 is a graph of pH verses channel number illustrating the results of Example 6.

In this example, narrow pH gradients were established that were stable over time. The narrow gradients were formed from a 5% ampholyte solution which yielded the same pH gradient as that produced in Example 4. After focusing, individual channels were collected, diluted to a 1% solution, distributed in all 8 channels of the isoelectric focusing device, and refocused. FIG. 18 illustrates the pH established by the subsequent focusing of the contents of channels 1 and 2. Data showing the results from focusing the other channels of the 5% run are not included, but they show similar narrow gradients. The gradients formed by the 1% runs have an average pH of the corresponding 5% channel fractionation.

It is currently believed that spiking is caused by ions entering the focusing cell due to electrolysis at the electrodes. During focusing, the high voltage at the electrodes surface causes electrolysis of water. At the cathode, the electrolysis reaction is:

$$2H_2O + 2e^- \rightarrow H_2 + 2OH^-$$

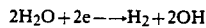

Hydroxyl ions ($OH^-$) are generated at the cathode during the electrolysis of water. Because conventional isoelectric focusing devices only use an anion selective membrane to separate the electrolyte from the focusing channels, it is suggested that $H^+$ ions pass through the anion selective membrane into the focusing chamber and move under the influence of the electric field into the channel bounding the anode, thereby eventually lowering the pH of that channel.

At the anode, the electrolysis reaction is:

$$2H_2O \rightarrow O_2 + 4H^+ + 4e^-$$

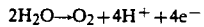

Hydrogen ions ($H^+$) are generated at the anode during the electrolysis of water. Because conventional isoelectric focusing devices only use a cation selective membrane to separate the electrolyte from the focusing channels, it is suggested that OH. ions pass through the cation selective membrane into the focusing chamber and move under the influence of the electric field into the channel bounding the cathode, thereby eventually raising the pH of that channel.

The use of a single bipolar membrane or dual anionic and cationic selective membranes to separate the electrolyte chambers and the focusing chambers dramatically reduces the movement of positively and negatively charged ions from the electrode compartments into the focusing cell compartments. As a result, almost no spiking or acid notching is observed over time so that very shallow pH gradients can be produced enabling high resolution separations.

From the foregoing, it will be appreciated that the present invention provides apparatus and methods for isoelectric focusing of amphoteric substances which inhibit spiking or acid notching.

Additionally, it will be appreciated that the present invention provides apparatus and methods for isoelectric focusing of amphoteric substances which enable narrow pH gradients to be obtained and maintained without significant spiking in the separation channels adjacent the electrodes.

Likewise, it will be appreciated that the present invention provides apparatus and methods for isoelectric focusing of amphoteric substances which provide high resolution separations.

It will be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An isoelectric focusing cell for separating amphoteric substances comprising:
   a plurality of inlet ports and a plurality of corresponding outlet ports;
   means for separating the flow of fluid which enters the isoelectric focusing cell through the inlet ports into a plurality of parallel focusing cell passageways such that fluid flowing through the inlet ports is channeled to corresponding outlet ports of each focusing cell passageway;
   an anode located within an anode chamber and a cathode located within a cathode chamber, said anode and said cathode being capable of applying an electric potential substantially transverse to the plurality of parallel focusing cell passageways; and
   means for minimizing both positive and negative ions contained within the anode chamber and within the cathode chamber from passing into the focusing cell passageways.

2. An isoelectric focusing cell as defined in claim 1, wherein the means for minimizing ions from passing into the focusing cell passageways comprises a bipolar membrane positioned between the anode chamber and at least one focusing cell passageway.

3. An isoelectric focusing cell as defined in claim 1, wherein the means for minimizing ions from passing into the focusing cell passageways comprises a bipolar membrane positioned between the cathode chamber and at least one focusing cell passageway.

4. An isoelectric focusing cell as defined in claim 1, wherein the means for minimizing ions from passing into the focusing cell passageways comprises a pair of bipolar membranes, one bipolar membrane being positioned between the anode chamber and at least one focusing cell passageway and the other bipolar membrane being positioned between the cathode chamber and at least one focusing cell passageway.

5. An isoelectric focusing cell as defined in claim 1, wherein the means for minimizing ions from passing into the focusing cell passageways comprises:
   an anion selective membrane and a cation selective membrane positioned between the anode chamber and at least one focusing cell passageway.

6. An isoelectric focusing cell as defined in claim 1, wherein the means for minimizing ions from passing into the focusing cell passageways comprises:
   an anion selective membrane and a cation selective membrane positioned between the cathode chamber and at least one focusing cell passageway.

7. An isoelectric focusing cell as defined in claim 1, wherein the means for minimizing ions from passing into the focusing cell passageways comprises:
   an anion selective membrane and a cation selective membrane positioned between the anode chamber and at least one focusing cell passageway; and
   an anion selective membrane and a cation selective membrane positioned between the cathode chamber and at least one focusing cell passageway.

8. An apparatus for isoelectric focusing of biological amphoteric substances within a fluid containing buffering components capable of establishing a stable pH gradient in an electric field, the apparatus comprising:
   an isoelectric focusing cell having a plurality of inlet ports and a plurality of corresponding outlet ports;
   a plurality of reservoirs arranged in pairs, each reservoir having a reservoir entrance to allow fluid flow into the reservoir and a reservoir exit to allow fluid flow out of the reservoir; each pair of reservoirs being coupled to a single inlet port of the isoelectric focusing cell and to the corresponding outlet port of the isoelectric focusing cell;
   means for directing fluid flow from each outlet port of the isoelectric focusing cell to the respective reservoir pair;
   means for directing fluid flow from each reservoir pair to the respective inlet port of the isoelectric focusing cell;
   means for alternating the fluid flow into and out of each reservoir of each reservoir pair such that when fluid flows from a first reservoir towards the isoelectric focusing cell, fluid flows from the isoelectric focusing cell towards a second of each reservoir pair such that after the first reservoir empties, fluid is directed to flow from the second reservoir of the respective reservoir pair towards the isoelectric focusing cell and fluid is simultaneously directed to flow into the first reservoir from the isoelectric focusing cell;
   an anode located within an anode chamber and a cathode located within a cathode chamber, said anode and said cathode being capable of applying an electric potential substantially transverse to the plurality of parallel focusing cell passageways; and
   means for minimizing ions contained within the anode chamber and within the cathode chamber from passing into the focusing cell passageways.

9. An apparatus for isoelectric focusing as defined in claim 8, wherein the means for minimizing ions from passing into the focusing cell passageways comprises a bipolar membrane positioned between the anode chamber and at least one focusing cell passageway.

10. An apparatus for isoelectric focusing as defined in claim 8, wherein the means for minimizing ions from passing into the focusing cell passageways comprises a bipolar membrane positioned between the cathode chamber and at least one focusing cell passageway.

11. An apparatus for isoelectric focusing as defined in claim 8, wherein the means for minimizing ions from passing into the focusing cell passageways comprises a pair of bipolar membranes, one bipolar membrane being positioned between the anode chamber and at least one focusing cell passageway and the other bipolar membrane being positioned between the cathode chamber and at least one focusing cell passageway.

12. An apparatus for isoelectric focusing as defined in claim 8, wherein the means for minimizing ions from passing into the focusing cell passageways comprises:

an anion selective membrane and a cation selective membrane positioned between the anode chamber and at least one focusing cell passageway.

13. An apparatus for isoelectric focusing as defined in claim 8, wherein the means for minimizing ions from passing into the focusing cell passageways comprises:
an anion selective membrane and a cation selective membrane positioned between the cathode chamber and at least one focusing cell passageway.

14. An apparatus for isoelectric focusing as defined in claim 8, wherein the means for minimizing ions from passing into the focusing cell passageways comprises:
an anion selective membrane and a cation selective membrane positioned between the anode chamber and at least one focusing cell passageway; and
an anion selective membrane and a cation selective membrane positioned between the cathode chamber and at least one focusing cell passageway.

15. An apparatus for isoelectric focusing of biological amphoteric substances within a fluid containing buffering components capable of establishing a stable pH gradient in an electric field, the apparatus comprising:
an isoelectric focusing cell constructed from a plurality of parallel focusing cell elements separated by a plurality of focusing cell separators, each said focusing cell element having a respective inlet port and a corresponding outlet port, each said focusing cell element having a fluid passageway therein;
a plurality of reservoirs arranged in pairs, each reservoir having a reservoir entrance to allow fluid flow into the reservoir and a reservoir exit to allow fluid flow out of the reservoir, each pair of reservoirs being coupled to the inlet port of a corresponding focusing cell element and to the outlet port of the corresponding focusing cell element;
means for directing fluid flow from each outlet port of the focusing cell elements to the respective reservoir pair;
means for directing fluid flow from each reservoir pair to the respective inlet ports of the focusing cell elements;
means for alternating the fluid flow into and out of each reservoir of each reservoir pair such that when fluid flows from a first reservoir towards the isoelectric focusing cell, fluid flows from the isoelectric focusing cell towards a second of each reservoir pair such that after the first reservoir empties, fluid is directed to flow from the second reservoir of the respective reservoir pair towards the isoelectric focusing cell and fluid is simultaneously directed to flow into the first reservoir from the isoelectric focusing cell;
an anode located within an anode chamber and a cathode located within a cathode chamber, said anode and said cathode being capable of applying an electric potential substantially transverse to the plurality of parallel focusing cell elements; and
a bipolar membrane separating the anode chamber from the focusing cell passageways and a bipolar membrane separating the cathode chamber from the focusing cell passageways, said bipolar membranes minimizing ions produced by the electrolysis of anolyte contained within the anode chamber and of catholyte contained within the cathode chamber from passing into the focusing cell elements.

16. A method for isoelectric focusing of amphoteric substances comprising the steps of:
passing fluid containing buffering components into an isoelectric focusing cell comprising:
a plurality of inlet ports, a plurality of corresponding outlet ports, and a plurality of isoelectric focusing cell passageways coupling each inlet port with a respective outlet port, said fluid being capable of establishing a stable pH gradient in an electric field;
a pair of electrodes, each located within respective electrode chambers, said pair of electrodes being capable of applying an electric potential substantially transverse to the focusing cell passageways; and
means for minimizing both positive and negative ions contained within at least one of the electrode chambers from passing into the focusing cell passageways;
applying an electric potential in a direction substantially transverse to the direction of fluid flow through the isoelectric focusing cell passageways, thereby establishing a stable pH gradient across the isoelectric focusing cell passageways; and
introducing an amphoteric substance to be analyzed into the fluid such that the amphoteric substance passes into the isoelectric focusing cell.

17. A method for isoelectric focusing of amphoteric substances as defined in claim 16, further comprising the steps of:
circulating fluid exiting the isoelectric focusing cell to a plurality of reservoirs arranged in pairs such that each outlet port of the isoelectric focusing cell is coupled to a pair of reservoirs and such that each pair of reservoirs is coupled to a corresponding inlet port of the isoelectric focusing cell; and
alternating the fluid flow into and out of each reservoir of each reservoir pair such that when fluid flows from a first reservoir into a respective inlet port of the isoelectric focusing cell, fluid flows from a corresponding outlet port of the isoelectric focusing cell into a second of each reservoir pair such that after the first reservoir empties, fluid is directed to flow from the second reservoir of the respective reservoir pair into the respective inlet port and fluid is simultaneously directed to flow into the first reservoir from the respective outlet port.

18. A method for isoelectric focusing as defined in claim 16, wherein the means for minimizing ions from passing into the focusing cell passageways comprises a bipolar membrane positioned between the anode chamber and at least one focusing cell passageway.

19. A method for isoelectric focusing as defined in claim 16, wherein the means for minimizing ions from passing into the focusing cell passageways comprises a bipolar membrane positioned between the cathode chamber and at least one focusing cell passageway.

20. A method for isoelectric focusing as defined in claim 16, wherein the means for minimizing ions from passing into the focusing cell passageways comprises a pair of bipolar membranes, one bipolar membrane being positioned between the anode chamber and at least one focusing cell passageway and the other bipolar membrane being positioned between the cathode chamber and at least one focusing cell passageway.

21. A method for isoelectric focusing as defined in claim 16, wherein the means for minimizing ions from passing into the focusing cell passageways comprises:

an anion selective membrane and a cation selective membrane positioned between the anode chamber and at least one focusing cell passageway.

22. A method for isoelectric focusing as defined in claim 16, wherein the means for minimizing ions from passing into the focusing cell passageways comprises:

an anion selective membrane and a cation selective membrane positioned between the cathode chamber and at least one focusing cell passageway.

23. A method for isoelectric focusing as defined in claim 16, wherein the means for minimizing ions from passing into the focusing cell passageways comprises:

an anion selective membrane and a cation selective membrane positioned between the anode chamber and at least one focusing cell passageway; and an anion selective membrane and a cation selective membrane positioned between the cathode chamber and at least one focusing cell passageway.

24. A method for isoelectric focusing as defined in claim 16, further comprising the step of periodically disrupting the fluid flow through the isoelectric focusing cell and the electric potential through the isoelectric focusing cell passageways such that the separation efficiency of the isoelectric focusing apparatus is improved.

25. A method for isoelectric focusing as defined in claim 16, further comprising the step of periodically disrupting the fluid flow through the isoelectric focusing cell such that the separation efficiency of the isoelectric focusing apparatus is improved.

26. A method for isoelectric focusing as defined in claim 16, further comprising the step of periodically disrupting the electric potential through the isoelectric focusing cell passageways such that the separation efficiency of the isoelectric focusing apparatus is improved.

* * * * *